| United States Patent [19] | [11] Patent Number: 4,921,679 |
| Martin et al. | [45] Date of Patent: May 1, 1990 |

[54] EXHAUST SYSTEM FOR LASER SURGERY

[76] Inventors: Juan N. Martin; John K. Martin, both of 2514 Old Fort Rd., Sugarland, Tex. 77479-1774

[21] Appl. No.: 313,013

[22] Filed: Feb. 21, 1989

[51] Int. Cl.$^5$ .............................................. B01D 50/00
[52] U.S. Cl. .................................... 422/169; 422/28; 422/33; 422/38; 422/4; 422/168
[58] Field of Search ...................... 422/1, 168, 28, 38, 422/4, 27, 292, 125, 126, 120, 33, 169

[56] References Cited

U.S. PATENT DOCUMENTS

| 3,721,525 | 3/1973 | Hortig et al. | 422/1 |
| 4,230,663 | 10/1980 | Forstrom et al. | 422/27 |
| 4,585,654 | 4/1986 | Landabura et al. | 422/1 |
| 4,643,876 | 2/1987 | Jacobs et al. | 422/28 |
| 4,661,126 | 4/1987 | Inagami et al. | 422/4 |
| 4,670,223 | 6/1987 | Delachapelle | 422/4 |

*Primary Examiner*—Christine M. Nucker
*Assistant Examiner*—Gregory R. Muir
*Attorney, Agent, or Firm*—Shlesinger & Myers

[57] ABSTRACT

In order to render harmless the aerosol laden smoke stream which results from the operation of medical lasers in or on mammalian bodies, the stream is moved in a closed circuit maintained at negative pressure. The circuit includes a container of sterilizing fluid to retain and destroy the larger aerosol particles and downstream of that container a chamber having an oxygen enriched atmosphere which is heated to a temperature sufficient to incinerate the remaining aerosol particles which are too small to filter. The thus purified stream is then cooled and released to ambient.

3 Claims, 2 Drawing Sheets

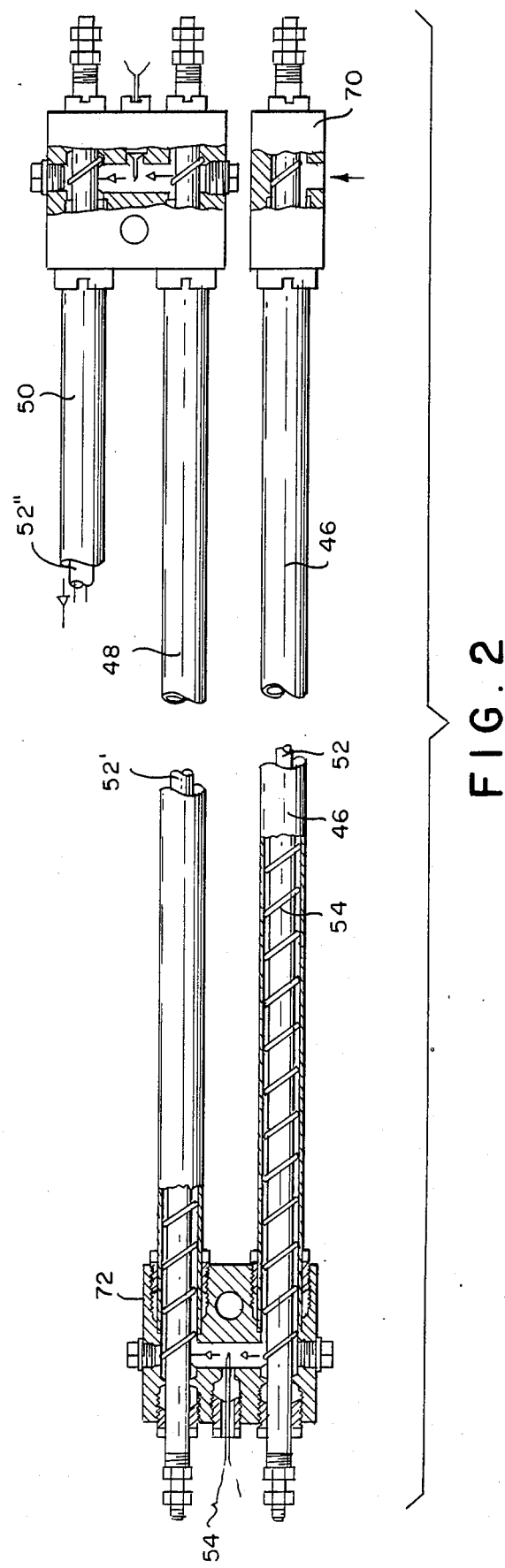

EXHAUST SYSTEM FOR LASER SURGERY

BACKGROUND OF THE INVENTION AND REFERENCE TO KNOWN PRIOR ART

The use of medical lasers in modern operating rooms is now commonplace because there are many advantages over the ordinary cutting tools, such as scalpels, such as instantaneous cauterization and reduction in the amount of bleeding. Unfortunately, there are certain undesirable side effects chief among which is the generation of a wide range of aerosol particles, the release of which into the operating theater is not only noxious but possibly hazardous to the health of all operating room personnel. One attempt at rectifying this condition may be found in the recently issued U.S. Pat. No. to Goodson et al 4,735,603, Apr. 5, 1988. This patent and some commercial laser smoke eliminators use filters having 0.3 micron openings which corresponds to 3000 Angstroms. These filters can retain larger size bacteria but definitely would not contain a virus of 30 Angstroms size. Since no one at this time seems to know exactly what viruses might be contained in the laser plume from an operating theater, and since it seems entirely possible that such plasma could contain non-filterable viruses which would definitely be hazardous to the operating room personnel, it would be desirable to employ a laser plume treatment system which would not filter the bacteria from the stream, but would also positively eliminate all virus particles including those as small as 30 Angstroms which cannot be filtered.

BRIEF SUMMARY OF THE INVENTION

In accordance with the present invention, we provide a system and apparatus for treatment of the laser smoke plume in a medical operating room which, first of all, maintains all of the products of the laser combustion under negative pressure to prevent any leakage from the system into the operating theater. The system which is completely fluid tight includes a first container of sterilizing fluid which acts as a filter and as a retainer for the larger aerosol particles which may contain bacteria and the like. The smaller aerosol particles which are odor-causing, which are unfilterable and which may also contain live viruses will of course pass through the container. These are then led to a combustion chamber which is electrically heated to a temperature sufficient to incinerate these particles and the incinerating is assisted by insuring that the chamber has an oxygen enriched atmosphere. The thus purified stream from the combustion chamber is then cooled in a heat exchanger and then released either to the operating theater ambient or to outside ambient as desired.

BRIEF DESCRIPTION OF THE DRAWINGS

FIG. 2 is a view partially in section of a preferred form of the combustion chamber.

DETAILED DESCRIPTION OF THE INVENTION

Figure 1:
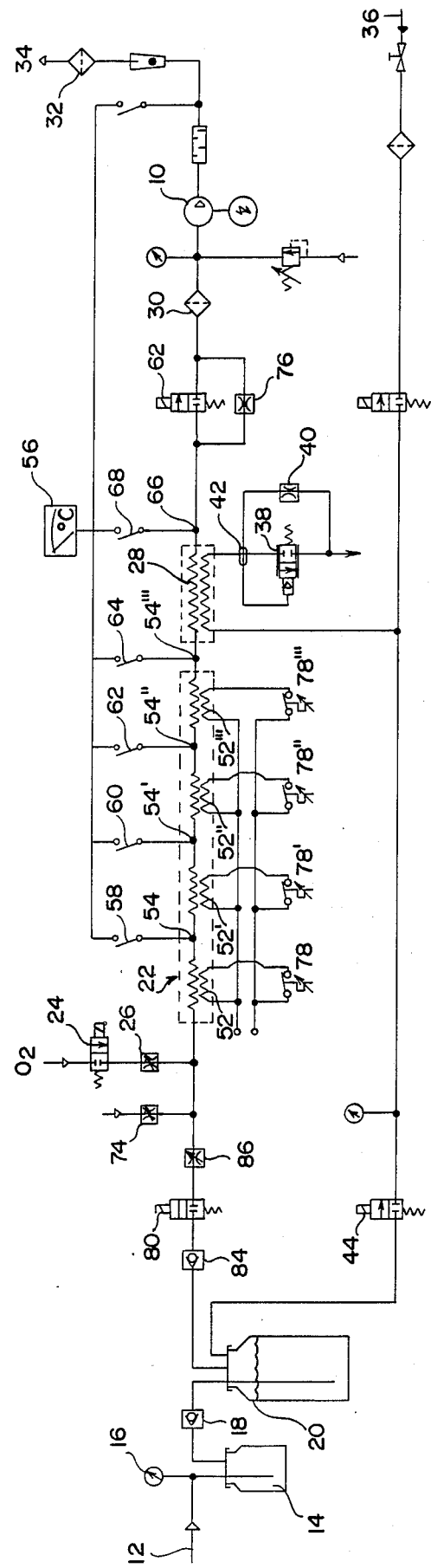
FIG. 1 is a system diagram embodying the features of the present invention.

Referring now to FIG. 1, assuming for purposes of description that the laser is being used within the peritoneal cavity of a human being, a vacuum pump 10 maintains the entire system under negative pressure to prevent any leakage of unprocessed or partially processed plume into the operating theater. A suction tube 12 is positioned within the body cavity adjacent the area of operation of the laser so that whenever the pump 10 is in operation, the products contained in the laser plume will be drawn into the line 12 and thus led to the container 14 which will catch and retain removed tissue and fluids for future study. A pressure gauge 16 may also be attached at this point to read pressure within the peritoneal cavity. As is well known in the medical-surgical field, the peritoneal cavity during surgery is kept inflated with a sterile inert gas such as $CO_2$ to a pressure of about 10" $H_2O$. The products created by operation of the laser are added to the inert gas which is then drawn into the line 12. The partial vacuum created by operation of the vacuum pump 10 must be promptly corrected by increased flow of inert gas into the cavity, and this is accomplished with an entirely separate apparatus which forms no part of the present invention and is not illustrated herein. The aerosol laden gaseous streams which exits from the container 14 is led through a check valve 18 into a second container 20 which is preferably filled at least partially with a sterilizing fluid such as hydrogen peroxide. The larger aerosol particles which may contain bacteria and the like are trapped in the container 20 and retained therein and rendered harmless by contact with the sterilizing fluid. The smaller aerosol particles pass through the container 20 and into a heating chamber 22. Oxygen is added to the mixture at this point through the valve 24 and the adjustable orifice 26 in order to enrich the oxygen content of the heating chamber 22 to promote incineration of the finer aerosols therein. The gaseous stream which exits from chamber 22 is completely sterile in view of the treatment in the container 20 and the incineration process in the chamber 22. Since its temperature at this point is high however, it is then passed through a heat exchanger cooler 28, filtered at 30 and 32 to trap any ash residue from the incineration process and finally released either to the operating theater ambient at 34 or to outside ambient as desired.

The heat exchanger cooler 28 is cooled by the passage of tap water from a source indicated at 36. The cooling water from the heat exchanger is dumped to a drain by a valve 38 and a fixed orifice 40, valve 38 being under the control of a temperature sensor 42. Tap water from the same source may be admitted to the container 20 under the control of the valve 44 as desired.

The foregoing description with reference to FIG. 1 describes the basic components of the system. FIG. 2 is a view partially in section showing a preferred embodiment of the heating chamber 22. As shown in this figure, the chamber is made up of a plurality (three are illustrated) of elongated tubular sections 46, 48 and 50 connected in series with each other so that the aerosol laden gas from the container 20 passes through the sections, one after another, beginning with the first section 46. Each section includes a rod shaped electrical heater 52 concentrically disposed within the outer tube and positioned therein by a spiral member 54. This structure therefore defines a spiral path to increase the effective length of the path of travel of the aerosol laden gases through the heating chamber.

As indicated in FIG. 1, there are preferably four sections of the heating chamber having heating elements 52, 52', 52" and 52''', respectively. Each of the individual heating elements is operatively associated with a thermocouple 54, 54', 54" and 54'''. These thermocouples are dual purpose devices since each serves to control the temperature of the individual heating units 52, and also, they may be used to indicate on meter 56 the temperature of the gases in each passage by selective closing of the switches 58, 60, 62 and 64. Another thermocouple 66 is associated with the outlet gas passage from the cooler 28, and here again, the temperature at this point may be read on the same meter 56 by closing the switch 68.

Again referring to FIG. 2, this illustrates the modular assembly by the various heating sections which make up the complete heating chamber 22 of FIG. 1. The first section is clamped between an entry fitting 70 and a crossover fitting 72. The latter provides a support for the first and second sections of the heating chamber as well as a path for travel of the gases from the first to the second and a housing for the thermocouple 54. It will be understood that a further crossover section identical to the one shown on 72 may be provided to support the opposite end of the section heating chamber section and a third section. The end of the last section in series will terminate in a piece identical to the entry member 70 illustrated in this figure.

Returning now to FIG. 1 for a description of the idling and active operation, the vacuum pump is operated continuously to maintain a continuous gas flow through the entire system, and this flow during the idling is limited by the fixed orifices 74 and 76. The thermocouples 54 provide control signals for the automatic temperature controls 78 for the individual heaters 52. At the same time, a limited flow of coolant through the heat exchanger 28 produces a signal at 42 which modulates the position of the coolant flow valve 38. When operation of the laser is started calling for ventilation of the body cavity, the valves 80, 24 and 62 are opened simultaneously which permits the vacuum pump 10 to withdraw gas from the body cavity through the solids separator 14, the safety check valve 18, the fluid sterilizer 20, a safety check valve 84 and valve 80 at a rate under the control of the adjustable valve 86. The flow control valve 74 permits a limited amount of atmospheric air to be added to the aerosol laden carrier gas, and additional air or oxygen is added through the valve 24 and the adjustable valve or orifice 26. The mixture of carrier gas $CO_2$ and laser produced aerosols together with the additional oxidizer are reacted in the thermal heating chamber to yield an end product of sterile $CO_2$. Therefore in the idling mode, the pilot gas flow with flow from the body cavity blocked maintains the control circuits of the thermal heating chamber activated and also maintains the cooler heat exchanger 28 of functioning in the idle mode.

While a preferred embodiment of the invention has been herein shown and disclosed, Applicants claim the benefit of a full range of equivalents within the scope of the appended claims.

We claim:

1. Apparatus for treating an aerosol laden smoke stream generated during laser surgery to render it harmless for release to the ambient comprising:
   (a) a closed, fluid tight circuit having an inlet and outlet;
   (b) means for maintaining said circuit under negative pressure;
   (c) said circuit including between said inlet and outlet the following elements serially connected in the order named:
      a container at least partially filled with a sterilizing fluid, to retain and destroy the larger aerosol particles;
      a heating chamber having means maintaining said chamber at a temperature sufficient to incinerate smaller unfilterable aerosol particles which pass through said container;
      means for oxygen enrichment of the atmosphere in said chamber;
      heat exchange means for cooling the stream exiting from said chamber; and
      means for releasing the thus treated stream to ambient.

2. Apparatus as defined by claim 1 including, upstream of said container, means for collecting and storing fluids and tissue contained in the stream.

3. Apparatus as defined by claim 1 in which said heating chamber comprises a plurality of serially connected sections, each section including a tubular outer casing having an elongated electrical heater therein and helical means positioning said heater centrally in said tube and defining an elongated helical flow path for gases being heated.

* * * * *